United States Patent
Pang

(10) Patent No.: US 7,901,557 B2
(45) Date of Patent: Mar. 8, 2011

(54) METHOD FOR MULTIPLEXED CAPILLARY ELECTROPHORESIS SIGNAL CROSS-TALK CORRECTION

(75) Inventor: Ho-Ming Pang, Ames, IA (US)

(73) Assignee: Advanced Analytical Technologies, Inc., Ames, IA (US)

( * ) Notice: Subject to any disclaimer, the term of this patent is extended or adjusted under 35 U.S.C. 154(b) by 102 days.

(21) Appl. No.: 12/426,317

(22) Filed: Apr. 20, 2009

(65) Prior Publication Data

US 2010/0264028 A1  Oct. 21, 2010

(51) Int. Cl.
    *G01N 27/447* (2006.01)
(52) U.S. Cl. ......................................... 204/452
(58) Field of Classification Search .......... 204/600–621, 204/450–470; 356/344; 422/70; 382/128, 382/129, 133, 134
See application file for complete search history.

(56) References Cited

U.S. PATENT DOCUMENTS

| | | | |
|---|---|---|---|
| 5,582,705 A | | 12/1996 | Yeung et al. |
| 5,682,038 A | * | 10/1997 | Hoffman ............... 250/458.1 |
| 6,788,414 B1 | | 9/2004 | Yeung et al. |
| 6,833,062 B2 | | 12/2004 | Kennedy et al. |
| 6,833,919 B2 | | 12/2004 | Kenseth et al. |
| 6,969,452 B2 | | 11/2005 | He et al. |
| 7,118,659 B2 | | 10/2006 | Kurt et al. |
| 7,402,817 B2 | * | 7/2008 | Gavrilov et al. ........... 250/459.1 |
| 7,497,937 B2 | | 3/2009 | Yeung et al. |
| 2006/0198558 A1 | * | 9/2006 | Riley et al. ................. 382/294 |

OTHER PUBLICATIONS

Ueno, K., et al., "Simultaneous Monitoring of DNA Fragments Separated by Electrophoresis in a Multiplexed Array of 100 Capillaries", Anal. Chem. 66:1424-1431 (1994).

* cited by examiner

*Primary Examiner* — Alex Noguerola
(74) *Attorney, Agent, or Firm* — McKee, Voorhees & Sease, P.L.C.

(57) ABSTRACT

The present invention provides a simple method to correct cross-talk, after the data have been generated. Adjacent signals are simply subtracted from the original observed signal with a repeating process. The data processing is stopped when a predefined condition is met. By this technique, cross-talk can be reduced from >5% to less than 0.1%. And as an additional advantage, this method provides a way to correct the cross-talk without the need to know which peaks are caused by the adjacent capillary signal.

3 Claims, 7 Drawing Sheets

METHOD FOR MULTIPLEXED CAPILLARY ELECTROPHORESIS SIGNAL CROSS-TALK CORRECTION

FIELD OF THE INVENTION

This invention relates to a method to correct the cross-talk caused from adjacent capillaries in multiplexed capillary electrophoresis (CE) systems.

BACKGROUND OF THE INVENTION

Capillary electrophoresis (CE) instruments use electric fields to separate molecules within narrow-bore capillaries (typically 20-100 µm internal diameter). By applying electrophoresis in a small diameter fused silica capillary column carrying a buffer solution, the sample size requirement is significantly smaller and the speed of separation and resolution can be increased multiple times compared to the slab gel-electrophoresis method. UV absorption and laser induced fluorescence are routinely used as the detection system for CE separation.

Applicant's assignee is the owner of several earlier U.S. patents related to CE systems, see Kensenth et al., U.S. Pat. No. 6,833,919; Kennedy, U.S. Pat. No. 6,833,062; He, U.S. Pat. No. 6,969,452; Kurt, U.S. Pat. No. 7,118,659; and Yeung, U.S. Pat. No. 7,497,937.

CE techniques are employed in numerous applications, including DNA sequencing, nucleotide quantification, mutation/polymorphism analysis, SDS-protein separation, and carbohydrate analysis. In order to improve sample throughput, multiple capillaries or channels were used to perform separations in parallel. For example, in one system a beam expander and a cylindrical lens are used to distribute laser light into a thin line that intersects the axes of the capillaries to provide laser induced fluorescent detection for a multiplexed CE system (K. Ueno et al., Anal. Chem., 66, 1424 (1994)). U.S. Pat. No. 5,582,705 used a laser as the excitation light source for fluorescence detection for a multiplexed CE system, while U.S. Pat. No. 6,788,414 revealed a method to perform UV absorption detection in a multiplexed CE system.

With all of the capillaries or channels illuminated at the same time, scattering, refraction, or reflection of light from neighboring channels will affect the detected channel. That is, detection in one capillary can be influenced by light absorption or fluorescence in the adjacent capillaries, thus affecting trace analysis. This phenomenon is referred to as cross-talk between adjacent capillaries. Cross-talk in the range of 1% to 10% could be observed in the previously mentioned inventions. For accurate analysis, cross-talk needs to be eliminated if possible.

There is, therefore, a need to reduce or eliminate the potentially negative cross-talk effects for trace analyte detection using CE. There are several prior art patented techniques to overcome the cross-talk issue. For example, U.S. Pat. No. 5,274,240 used a mechanical stage to translate the capillary bundle to observe one capillary at a time. U.S. Pat. No. 5,324,401 used individual optical fibers to collect emission light from each capillary to eliminate cross-talk. U.S. Pat. No. 5,790,727 used a waveguide to collect the fluorescent signal to reduce cross-talk. Yet another U.S. Pat. No. 7,340,048 taught use of a mask to block the unwanted scattering light to reduce the cross-talk from the adjacent capillaries. Although these various implementations of different optical design in the hardware to reduce the cross-talk are effective, the cost and the complication of the hardware designs are high. There is, therefore, a continuing need to develop less expensive alternate methods of eliminating cross-talk without increasing instrument complexity or cost. This invention has its primary objective fulfilling this need.

SUMMARY OF THE INVENTION

The present invention provides a simple method to correct cross-talk, after the data have been generated. Adjacent signals are simply subtracted from the original observed signal with a repeating process. The data processing is stopped when a predefined condition is met. By this technique, cross-talk can be reduced from >5% to less than 0.1%. And as an additional advantage, this method provides a way to correct the cross-talk without the need to know which peaks are caused by the adjacent capillary signal.

DETAILED DESCRIPTION OF THE INVENTION

Figure 1:
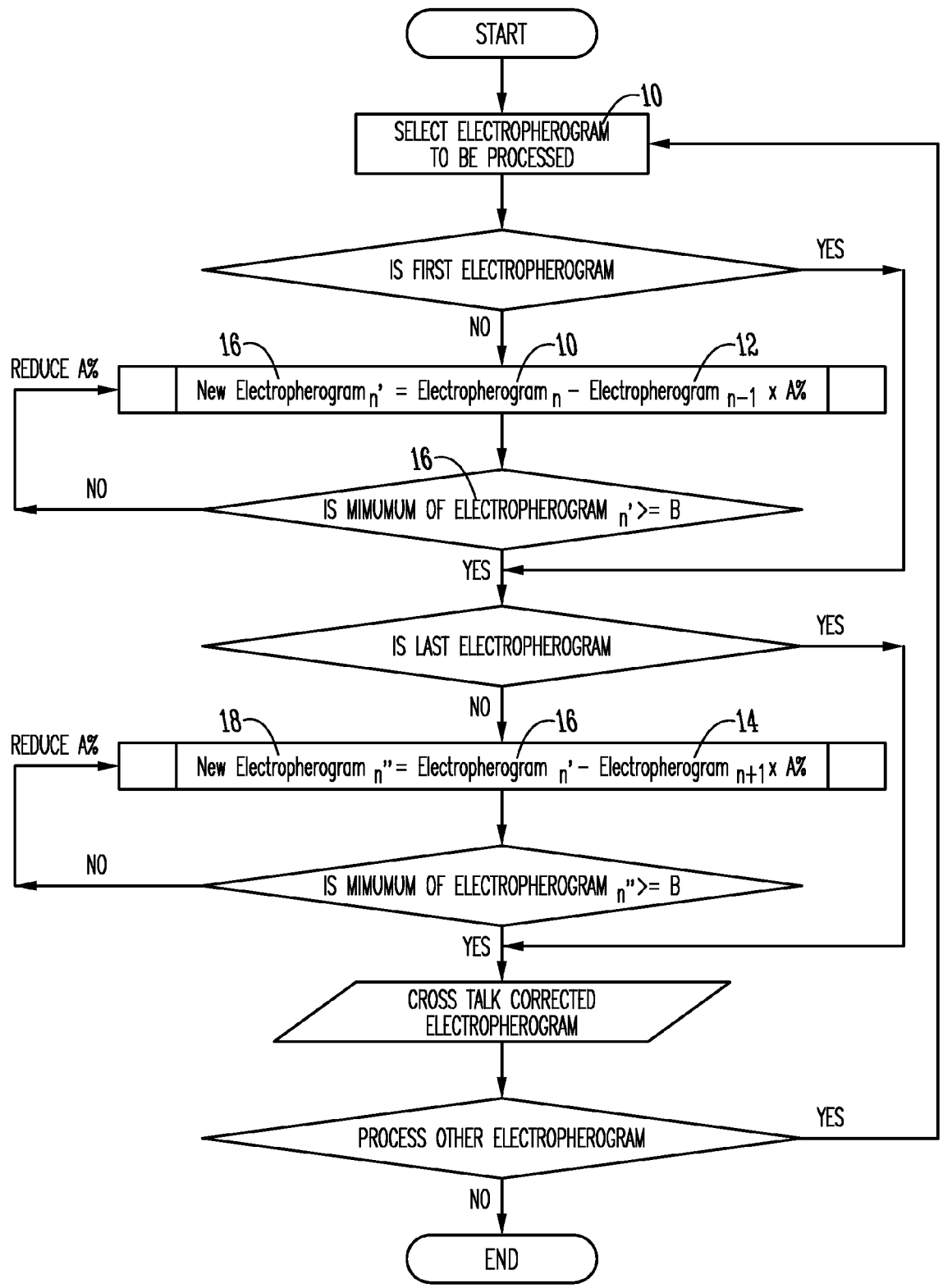
FIG. 1 is a method flow chart to illustrate the process of the present invention.

A specific embodiment of the invention is described in connection with FIG. 1. It is, however, to be understood FIG. 1 is exemplary only. The embodiment is however described in sufficient detail to enable those skilled in the art to practice the invention, and it is to be understood that other embodiments may be utilized and that structural and functional changes may be made without departing from the spirit and scope of the present invention.

The present invention recognizes that cross-talk from the adjacent capillary signal is basically an imposed small percentage of signal of the adjacent capillary into the capillary signal of interest. One could therefore reduce or eliminate the cross-talk by simply subtracting the adjacent capillary signal from the signal of interest, if the corrected percentage of adjacent capillary signal is used. However, in order to know the exact percentage of adjacent capillary signal to subtract out for correction, it is required to know which peaks of an electropherogram are due to cross-talk. One could certainly compare peak by peak in between the electropherogram of interest and adjacent capillary electropherogram to find out which peak(s) is due to cross-talk and then removed it accordingly. However, this process would be time consuming and difficult to implement. The present invention provides an easy approach that requires no prior knowledge of which ones in fact are cross-talk peaks. In the methodology of the present invention, the adjacent signals are simply subtracted from the original observed signal in an iterated process. The data processing is stopped when a predefined condition is met. In this way, cross-talk can be reduced from typically >5% to less than 0.1%, especially when B is a number between −0.1% and −0.5%.

FIG. 1 shows the present invention methodology in flow chart format. The basic process is described in connection with the FIG. 1 flow chart. All electropherograms used in this invention are baseline corrected electropherograms to remove the signal offset or drifting before further data processing. The electropherogram of interest ($10$) (electropherogram$_n$) is selected to perform the cross-talk reduction. Baseline corrected electropherogram$_{n-1}$ ($12$), electropherogram$_n$ ($10$), and electropherogram$_{n+1}$ ($14$) are the electropherograms from three adjacent capillaries. This baseline correction process sets all electropherogram signal values to $\geq 0$. Electropherogram$_n$ ($10$) is the center capillary electropherogram of the three adjacent capillaries. Electropherogram$_{n-1}$ ($12$) and electropherogram$_{n+1}$ ($14$) are the electropherograms from the capillaries next to the capillary with electropherogram$_n$ ($10$). One of the adjacent capillary electropherogram (electropherogram$_{n-1}$ ($12$), or electropherogram$_{n+1}$ ($14$)) signal is multiplied with a factor (A %) with a value in between 100% and 0%. For example, if the cross-talk signal is no more than 10% of the adjacent electropherogram signal, one could set the factor to be 20%. Or one could use 100% of the adjacent capillary electropherogram signal for subtraction. This resulting smaller electropherogram$_{n-1}$ ($12$) signal or full scale signal is subtracted from the electropherogram$_n$ ($10$). The new electropherogram$_{n'}$ ($16$) value is examined. If there is no negative value, then one could assume that there is no cross-talk from the capillary electropherogram$_{n-1}$ ($12$). The iterate process is stopped and one then goes to the next step. However, if the electropherogram$_{n'}$ ($16$) signal has negative value and the valve is smaller than the pre-determined value (B), the previously described process repeats with a reduced A % value until the smallest value of electropherogram$_{n'}$ ($16$) no longer smaller than the value B. The resulting electropherogram$_{n'}$ ($16$) will perform another cross-talk correction from another adjacent capillary electropherogram based on the same process described previously to generate cross-talk corrected electropherogram$_{n''}$ ($18$). In addition, for the first or last capillary electropherogram, only one adjacent capillary electropherogram cross-talk should be corrected.

Figure 2:
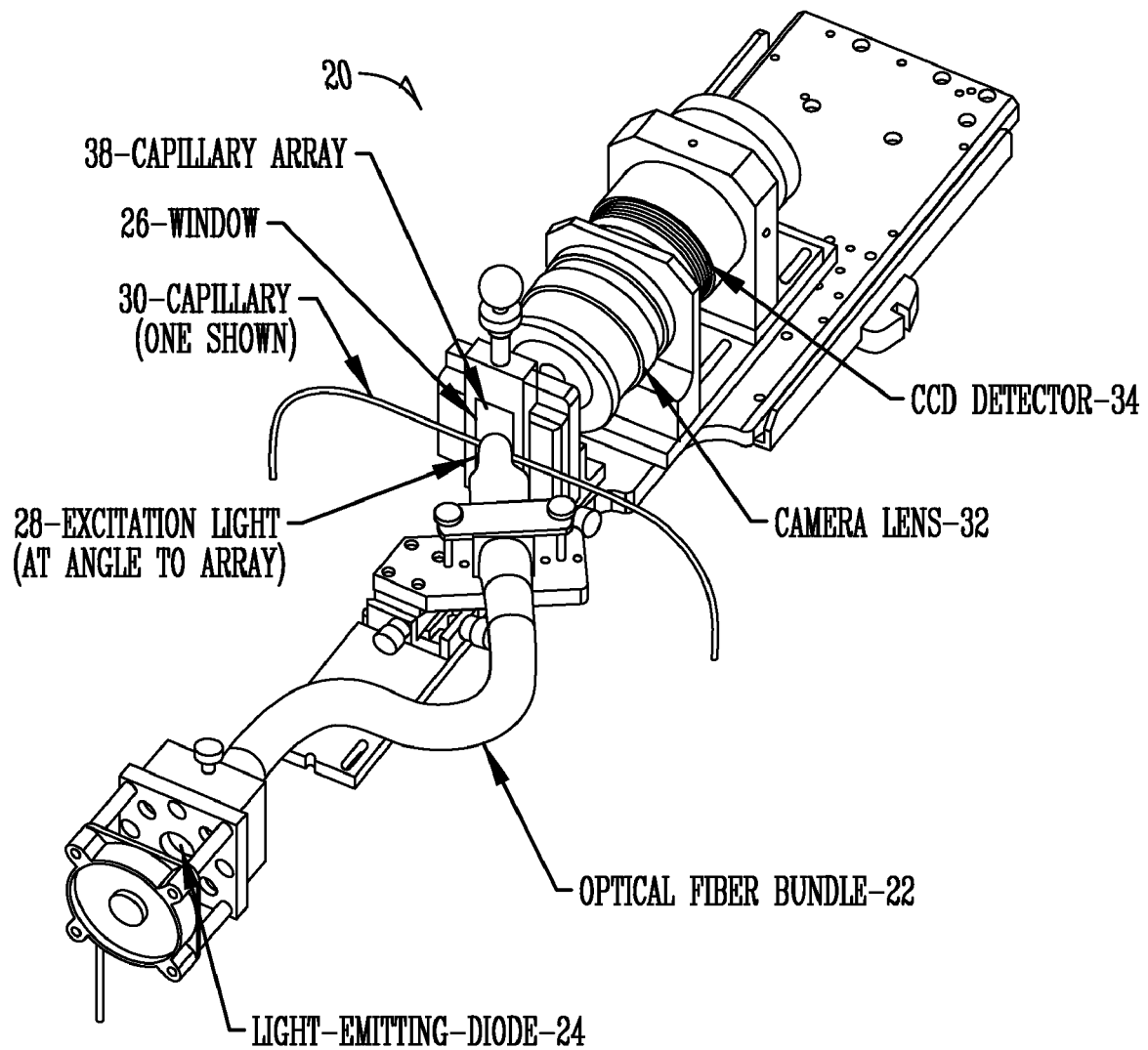
FIG. 2 shows a perspective view of a typical parallel CE system.

FIG. 2 shows the schematic view of a multiplexed CE system with fluorescence detection system that was used to generate the electropherograms of the example. The detail of description of the system setup can be found in our published U.S. patent application Ser. No. 11/299,643, Publication U.S. 2007/0131870 A1, which is incorporated herein by reference. A high throughput detection system referred to generally as $20$ is based upon an optical fiber bundle $22$ used to deliver a single LED light source $24$, instead of an expensive high-powered laser in a multichannel detection system, through a window $26$, at preferably an acute angle, the angle being most preferably 45°. The angle of this system is illustrated at $28$, the window at $26$ and one capillary at $30$. An optical camera lens $32$ is used for collecting the fluorescent signal and is recorded on a two-dimensional imaging array detector such as a charged couple device (CCD) detector $34$. In addition, pixel binning from the detector along the detection window signal is used to improve the signal to noise ratio without losing separation resolution. When imaging the fluorescent signal from the detection windows of the capillary array $38$ to the CCD detector $34$, each capillary emission signal will cover more than one pixel on the CCD detector $34$. The fluorescent light from the detection window irradiates onto multiple pixels of the CCD detector. By combining the corresponding signals together (horizontally and vertically), a higher signal to noise ratio of the detection signal can be obtained.

EXAMPLE

The following example is offered to illustrate but not limit the process of this invention.

Figure 3A:
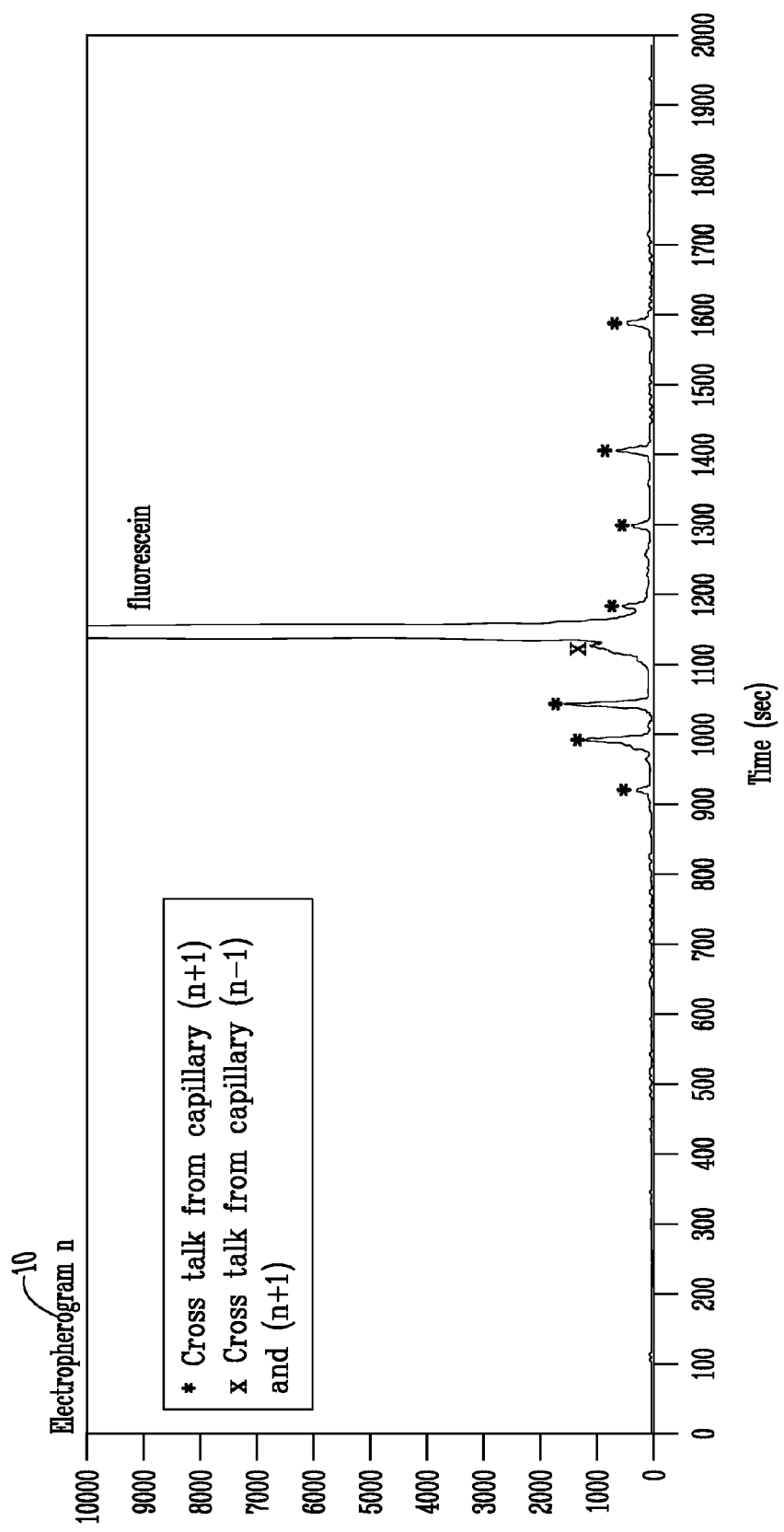
FIGS. 3A, 3B, and 3C show three adjacent capillaries' observed signal electropherograms.
Figure 3B:
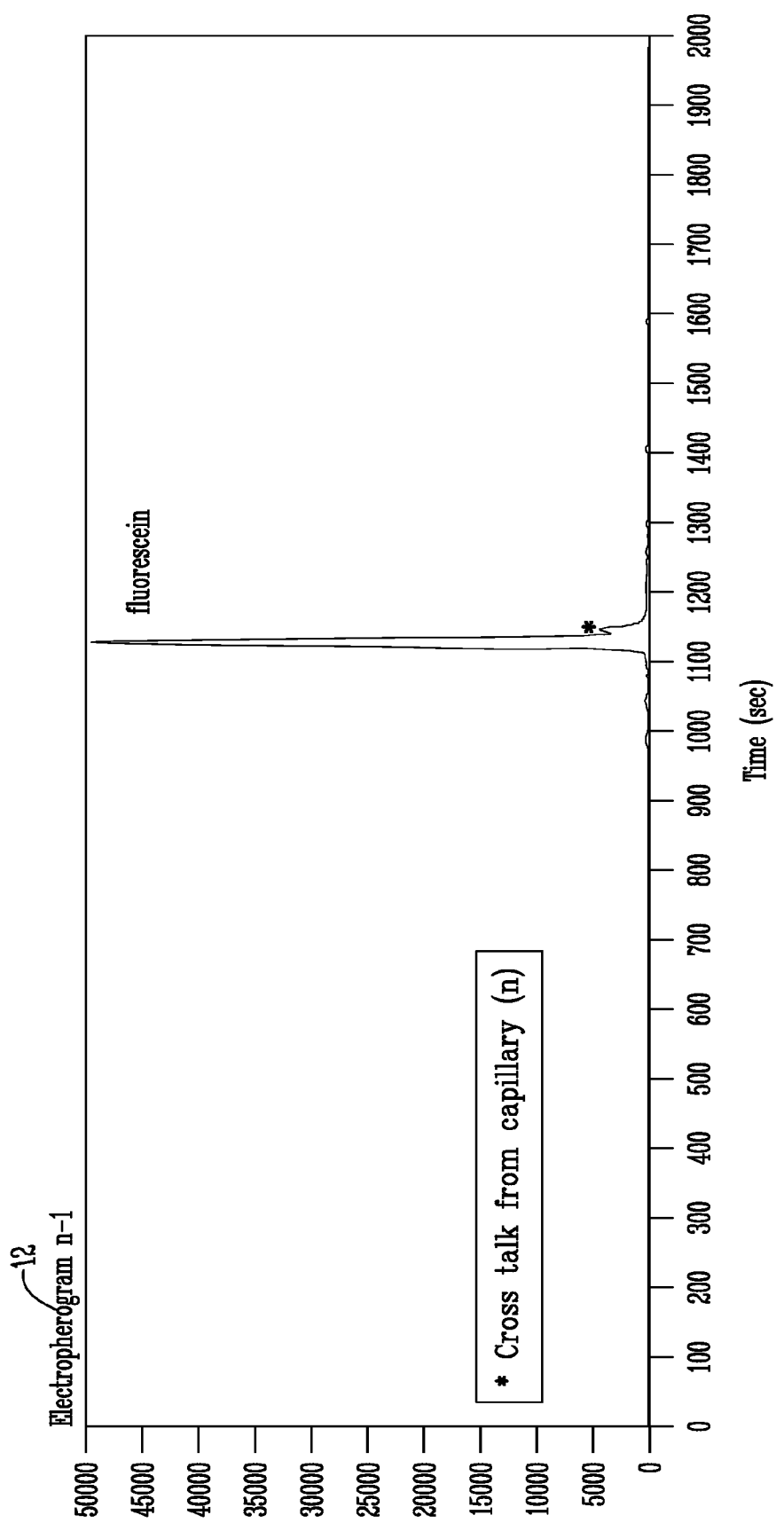
Figure 3C:
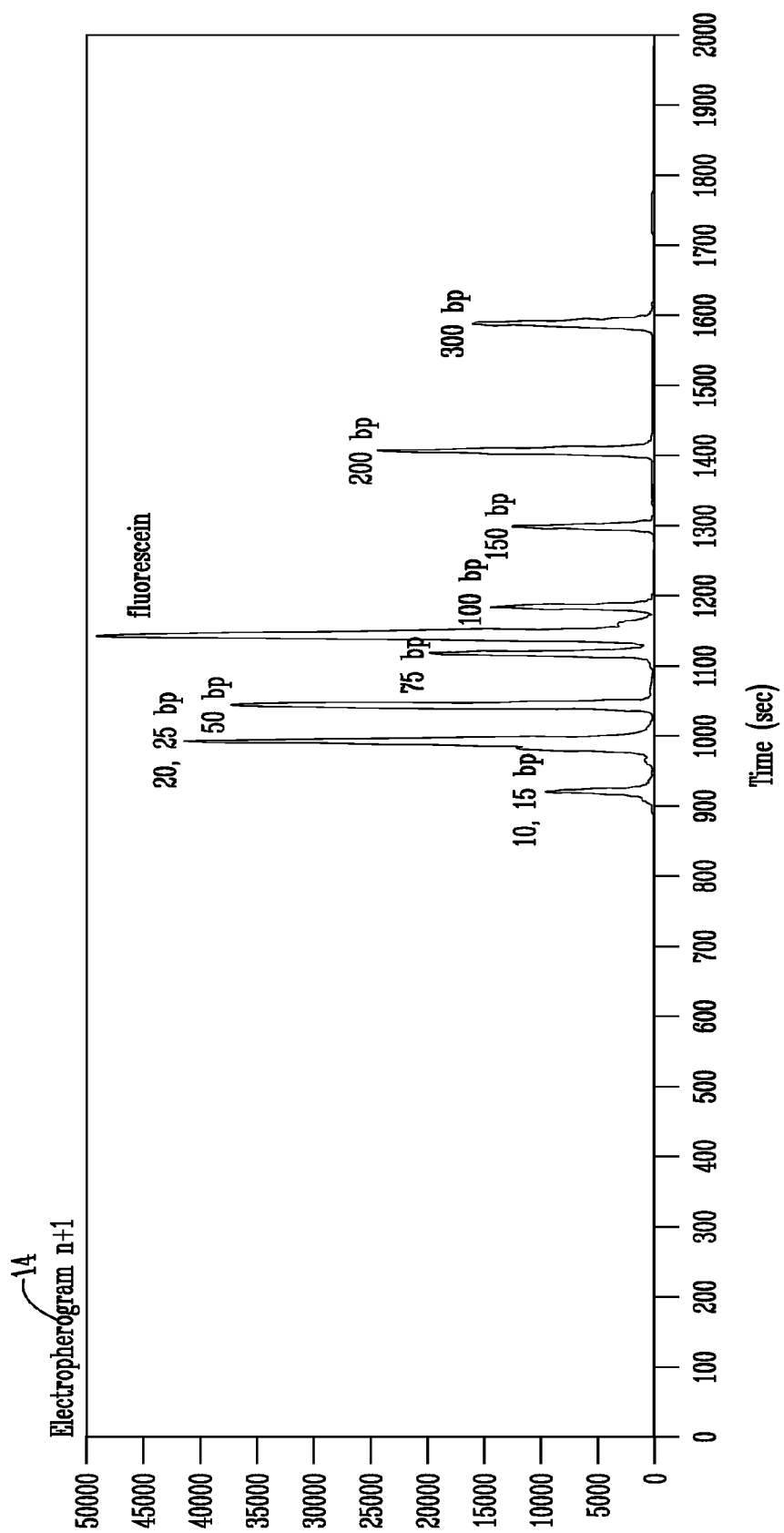

The multiplexed system described in FIG. 2 was utilized to generate electropherograms, FIGS. 3A, 3B and 3C to illustrate the cross-talk correction process. What kind of precise hardware or system (here FIG. 2) that is used to generate the signal is not important, as long as parallel capillaries or channels are used for the simultaneous detection. The capillaries are filled with a sieving matrix that contained a dye such as ethidium bromide that binds to the dsDNA and that fluoresces when excited by the light source. The CCD detector $34$ recorded the fluorescence output from the detection windows during the course of electrophoresis separation. Software algorithms were used to extract and re-construct the signal output as electropherograms 3A, 3B, and 3C, i.e., signal intensity change vs. time for each capillary.

FIGS. 3A, 3B, and 3C depict three electropherograms obtained from three adjacent capillaries. For illustrative purposes, capillary n–1 ($12$) and n ($10$) were injected with fluorescein dye as sample, while capillary n+1 ($14$) was injected with DNA ladder and fluorescein mixture as sample. It was obvious for the electropherogram obtained for capillary n ($10$), significant cross-talk (up to 5%) was observed from both adjacent capillaries (n–1 ($12$) and n+1 ($14$)).

Figure 4:
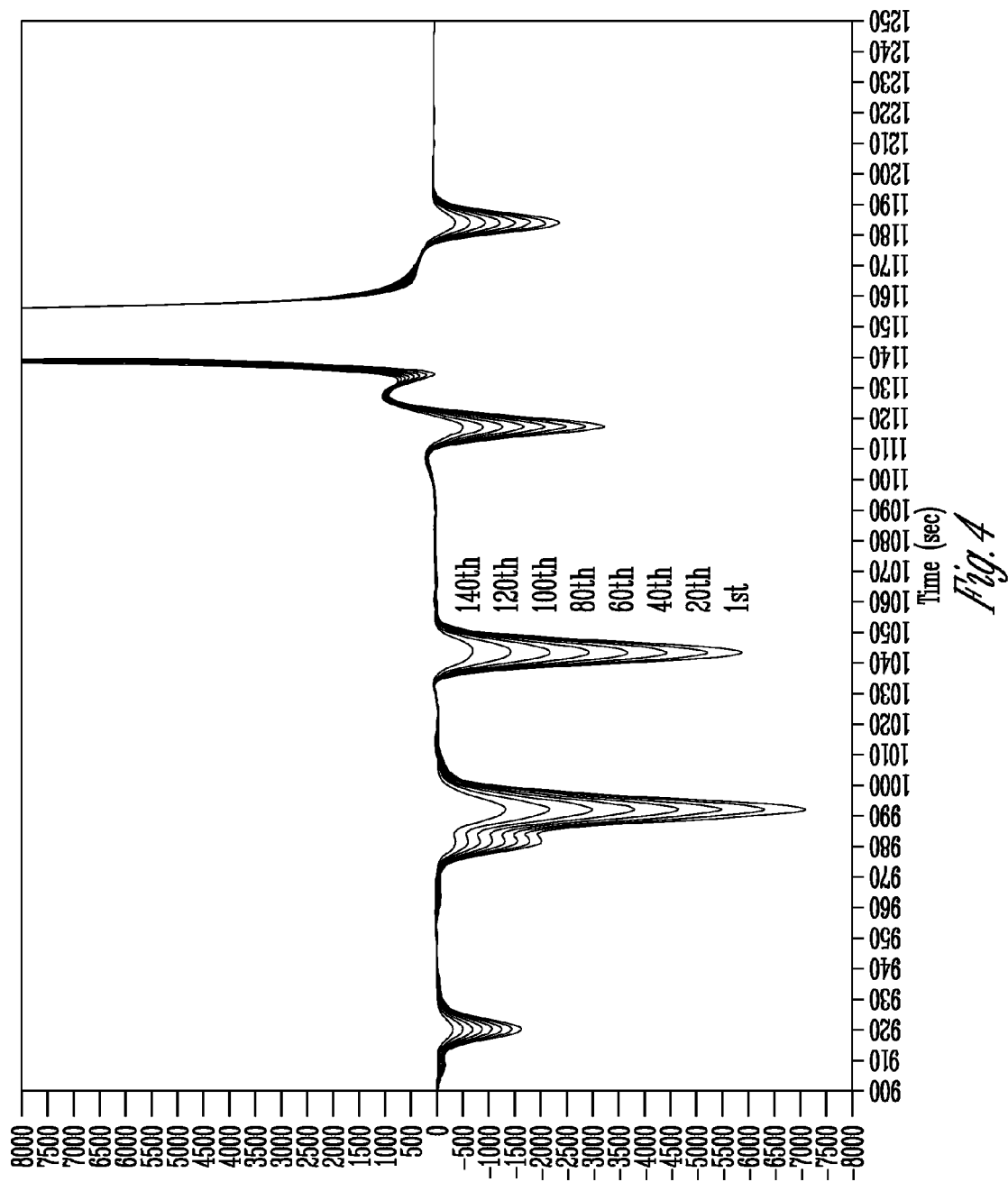
FIG. 4 shows the intermediate step results of the processed electropherogram.

FIG. 4 depicts the intermediate result observed by using the present invention methodology. FIG. 4 shows the process of correcting the cross-talk capillary n electropherogram ($10$) from capillary n+1 ($14$) electropherogram. Since in most cases, the cross-talk is less than 10%, one could use 20% of the capillary n+1 ($14$) electropherogram signal as the starting point for correction. The $1^{st}$ trace shows the first iterate process result of 20% electropherogram$_{n+1}$ ($14$) signal subtracted from electropherogram$_n$ ($10$). Because of the over-correction, excess negative peaks are observed. One could reduce the electropherogram$_{n+1}$ ($14$) signal before the subtraction for the $2^{nd}$ iterate process. For example, the $2^{nd}$ iterate process could then subtracted 19.9% of electropherogram$_{n+1}$ ($14$) signal from the electropherogram$_n$ ($10$). The $20^{th}$ trace shows the $20^{th}$ iterate process result, while reducing the electropherogram$_{n+1}$ ($14$) signal to 18.1%. Since the percentage of n+1 ($14$) electropherogram signal was reduced, a slightly less over-correction was observed here. The $40^{th}$, $60^{th}$, (see FIG. 4) and so on show the corresponding result when the percentage of electropherogram$_{n+1}$ ($14$) is gradually reduced to 16.1%, 14.1% and so on when each step reduced the electropherogram$_{n+1}$ ($14$) signal by additional 0.1% for each correction process. The subtraction process is stopped when the minimum value of the subtracted electropherogram is larger than a preset value (B). For example, one could use negative 0.1% of the adjacent capillary's electropherogram maximum value, or an arbitrary value, such as negative 10, as the pre-defined value to stop the process. Generally, if the selected B value is within the range of –0.10% to –0.50% cross-talk can be reduced from about 4%-5% down to 0.1%.

Figure 5:
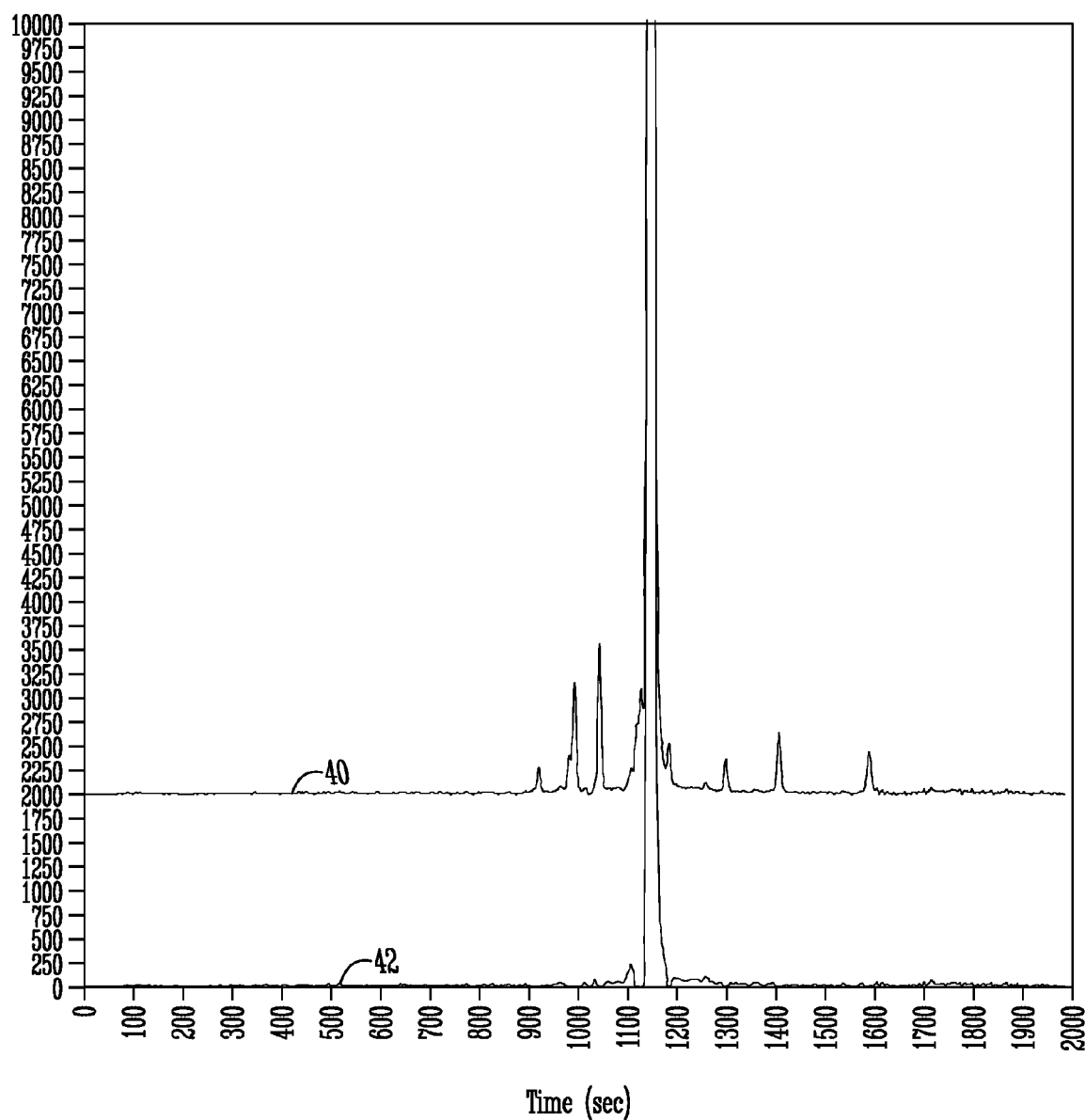
FIG. 5 shows the final result of the cross-talk corrected electropherogram using the present invention vs. original electropherograms of FIG. 3A.

FIG. 5 shows the final result after the cross-talk correction data processing from both adjacent capillaries electropherograms. The upper trace $40$ was the original signal while the lower trace $42$ showed the processed signal. The upper trace $40$ was offset by 2000 count for display purpose. The cross-talk was virtually eliminated. The result indicated that this data processing is effective to reduce/eliminate the cross-talk interference. In FIG. 5, one can easily observe a small impurity signal at about 1110 second on the cross-talk corrected electropherogram (the lower trace $42$) while the impurity signal was obscured by the cross-talk signal.

The invention has been shown and described above with the preferred embodiments, and it is understood that many modifications, substitutions, and additions may be made which are within the intended spirit and scope of the invention. From the foregoing, it can be seen that the present invention accomplishes at least all of its stated objectives.

What is claimed is:

1. A method of correcting multiplexed capillary electrophoresis (CE) electropherograms for cross-talk, comprising:

preparing an observed signal electropherogram for a selected capillary of a multi-capillary electrophoresis (CE) system;

preparing an observed signal (CE) electropherogram for the adjacent capillaries on each side of the selected capillary;

selecting an arbitrary percentage that is less than 100% for designation as A % that is multiplied with the observed selected signal, the product being subtracted out from the observed selected signal for each adjacent capillary;

repeating the A % multiplication with reduced A % value, and subtraction out process as long as it gives a negative value, and/or until the subtracted value is larger than an arbitrary preset B value:

preparing a corrected multiplexed capillary electrophoresis electropherogram.

2. The process of claim 1 wherein the A % value is from 5% to 20% of the adjacent capillary signal.

3. The process of claim 2 wherein the B value is between −0.1% and −0.5% of the adjacent capillary signal.

* * * * *